United States Patent
Liao et al.

(10) Patent No.: US 10,472,317 B2
(45) Date of Patent: Nov. 12, 2019

(54) DIOCTYL TEREPHTHALATE PLASTICIZER AND METHOD OF ENHANCING REACTION EFFICIENCY IN PROCESS FOR PRODUCING THE SAME

(71) Applicant: NAN YA PLASTICS CORPORATION, Taipei (TW)

(72) Inventors: Te-Chao Liao, Taipei (TW); Jung-Jen Chuang, Taipei (TW); Hsun-Min Lin, Taipei (TW)

(73) Assignee: NAN YA PLASTICS CORPORATION, Taipei (TW)

( * ) Notice: Subject to any disclaimer, the term of this patent is extended or adjusted under 35 U.S.C. 154(b) by 0 days.

(21) Appl. No.: 16/008,164

(22) Filed: Jun. 14, 2018

(65) Prior Publication Data

US 2018/0362440 A1 Dec. 20, 2018

(30) Foreign Application Priority Data

Jun. 19, 2017 (TW) .............................. 106120434 A

(51) Int. Cl.
*C07C 67/08* (2006.01)
*C07C 69/82* (2006.01)

(52) U.S. Cl.
CPC .............. *C07C 67/08* (2013.01); *C07C 69/82* (2013.01)

(58) Field of Classification Search
CPC .................. C07C 67/08; C07C 69/82
See application file for complete search history.

(56) References Cited

U.S. PATENT DOCUMENTS

2007/0038001 A1* 2/2007 Cook ...................... C07C 67/08
560/99
2016/0137582 A1* 5/2016 Frey ........................ C07C 67/08
560/198

FOREIGN PATENT DOCUMENTS

KR    20130067510     *  6/2013
WO    WO2014/185872   * 11/2014

OTHER PUBLICATIONS

KR20130067510 translated (Year: 2013).*

* cited by examiner

*Primary Examiner* — Yevgeny Valenrod
*Assistant Examiner* — Blaine G Doletski
(74) *Attorney, Agent, or Firm* — Li & Cai Intellectual Property (USA) Office

(57) ABSTRACT

A method for enhancing reaction efficiency of a terephthalate plasticizer involves using a homogenizer to fine PTA to slurry having a particle size of 80-110 μm, and esterifying the PTA slurry with a C6-C10 alcohol in the presence of a titanium-based catalyst. The reactivity is enhanced by more than 37.5%, and the terephthalate plasticizer so synthetized is low-odor and has a purity of more than 99.5% as well as good physical properties such as acid value, color, and index of refraction.

6 Claims, 1 Drawing Sheet

DIOCTYL TEREPHTHALATE PLASTICIZER AND METHOD OF ENHANCING REACTION EFFICIENCY IN PROCESS FOR PRODUCING THE SAME

BACKGROUND OF THE INVENTION

1. Field of the Invention

The present invention relates to dioctyl terephthalate plasticizers, and more particularly to a method of enhancing reaction efficiency and reducing reaction time at least by 37.5% in a process for producing the dioctyl terephthalate plasticizers.

2. Description of Related Art

Dioctyl terephthalate (DOTP) is an important phthalate-free plasticizer and is environmentally friendly. DOTP plasticizers are synthesized by esterifying purified terephthalic acid (hereinafter referred to as PTA) and 2-ethylhexanol (hereinafter referred to as 2-EH). PTA is not soluble in 2-EH and normal solvents, so the esterification is a heterogeneous solid-liquid reaction, where PTA tends to have sedimentation and agglomeration. Besides, due to insolubility of PTA in 2-EH, esterification can only happen at the boundary between PTA and 2-EH, making the reaction extremely slow and time-consuming. Currently, industrial production of DOTP mainly uses titanate as the catalyst, and the reaction takes at least 5 hours. Hence, the incompatibility between PTA and 2-EH and the prolonged synthesis time have long been unsolved problems.

For improving reactivity in process for producing DOTP, a known method for catalytically synthesizing diisooctyl terephthalate uses ionic liquid of quaternary ammonium salt as a co-catalyst and a hydrotropic agent. However, since this ionic liquid may lead to side reaction or interact with catalysts, a purification step involving long standing time is required for separation, which can disadvantageously complicate and prolong the manufacturing process. US Patent Application publication 2002028963-A1 discloses a process for preparing carboxylic esters wherein water is removed by azeotropic distillation together with an alcohol. While this known approach does save some time for esterification, the decrease is only 9-11% and not significant.

SUMMARY OF THE INVENTION

In view of this, the objective of the present invention is to improve reactivity in process for producing dioctyl terephthalates. PTA is in advance homogenized into a fine particle with homogenizer. As a result, PTA is unlikely to agglutinate, and the reaction liquid is unlikely to bubble and attach to walls of the reaction tank. Particularly, the beforehand homogenization-processed PTA has its surface become wrinkles, which provide increased surface area and facilitate permeation of 2-EH for reaction inside PTA, thereby enhancing reactivity and shortening reaction time. With the parameters for normal esterification, namely a pressure of between minus 30 mbar and the atmospheric pressure (i.e., −30 to 1013 mbar) and 180-250° C., the method can make the reaction time decreased at least by 37.5-50%. The DOTP plasticizer so synthesized has its purity higher than 99.5%, and has fair physical properties, including acid value, color, and index of refraction. The disclosed method advantageously helps to improve productivity and save energy, and the resulting DOTP plasticizer is low-odor.

The synthesis components, namely PTA and a straight-chain or branched-chain alcohol containing 6 to 10 carbon atoms (abbreviated as C6-C10 alcohol), are mixed as a PTA slurry and fined in a homogenizer to the extent that the PTA in the slurry has a particle size of 80-110 μm and has its specific surface area increased by 5-11%. The fined slurry is then pumped to the reaction tank to react with an excessive alcohol for esterification. The method of enhancing reaction efficiency and reducing reaction time in a process for producing the DOTP comprises steps of:

(1) making purified terephthalic acid (PTA) and a C6-C10 alcohol mixed in a weight ratio of 1:0.8-1.5 and processed in a homogenizer for 2-8 hours to form a PTA slurry having a PTA particle size of ranging between 80 and 110 μm;

(2) taking the PTA slurry of Step (1) of 75-107 wt % and taking additional said C6-C10 alcohol of 30-85 wt % (preferably, 35-65 wt %) as the components, both based on a total weight of the final DOTP plasticizer of Step (5), wherein the C6-C10 alcohol used in Step (1) and in this step is one or more selected from the group consisting of 2-ethylhexanol (2-EH), isononyl alcohol (INA) and isodecyl alcohol;

(3) taking a titanium-based catalyst of 0.1-2.0 wt % as an esterification catalyst, based on the total weight of the final DOTP plasticizer of Step (5);

(4) esterifying the components of Step (2) in presence of the esterification catalyst of Step (3) at a pressure of ranging between −30 and 1013 mbar and a temperature of ranging between 200 and 250° C. for 2-3 hours to form a reaction mixture; and (5) after esterification, neutralizing the reaction mixture with an aqueous solution of alkaline metal hydroxide that contains a hydroxide mixture of 5-20 wt %, until the reaction mixture having its acid value reduced to below 0.07 mgKOH/g, and then performing removal of the residual alcohol, drying and filtration, as to obtain the final DOTP plasticizer.

DETAILED DESCRIPTION OF THE INVENTION

Figure 1:
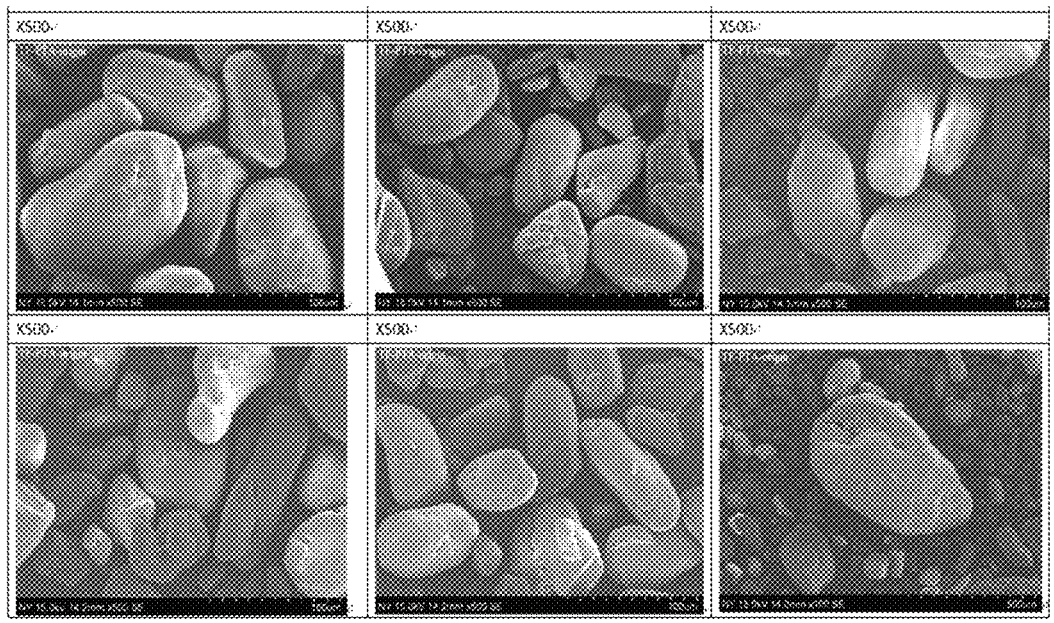
FIG. 1 is a SEM image of the surface of un-fined PTA.

The method for making a dioctyl terephthalate (DOTP) plasticizer according to the present invention involves using PTA and a C6-C10 alcohol mixture as reaction components. The PTA and the C6-C10 alcohol are mixed in a weight ratio of 1:0.8-1.5 and processed in a homogenizer for fining process. Then, with the presence of a titanium-based catalyst, the fined mixture is esterified. After esterification, an aqueous solution of alkaline metal hydroxide is used for neutralization reaction, and after removal of the residual alcohol, drying, filtration and purification, the final an esterified terephthalate plasticizer with high purity and good color is obtained.

The method of enhancing reaction efficiency and reducing reaction time by 37.5-54.5% in a process for producing the DOTP plasticizers of the present invention comprises the following steps:

1) Preparation of PTA slurry: making PTA and a C6-C10 alcohol mixed in a weight ratio of 1:0.8-1.5 to form a PTA slurry and processed in a homogenizer for 2-8 hours to allow the PTA to have a PTA particle size of ranging between 80 and 110 μm and its specific surface area increased by 5-10%, preferably 80-100 μm and 7-10%, wherein a particle size smaller than this can lead to agglutination and is undesirable;

2) taking the PTA slurry of step 1) of 85-107 wt % and taking a C6-C10 alcohol of additional 30-85 wt % (preferably, 35-65 wt %) as the components, both based on a total weight of the final DOTP plasticizer of step 5);

3) taking a metal catalyst of 0.1-2.0 wt % as an esterification catalyst, based on the total weight of the final DOTP plasticizer of step 5);

4) esterifying the components of Step (2) in the presence of the metal catalyst at a pressure of ranging between −30 and 1013 mbar and a temperature of between 200 and 250° C. for 2-3 hours, until the acid value of the reaction mixture becomes lower than 0.1 mgKOH/g;

5) after esterification, neutralizing the reaction mixture with an aqueous solution of alkaline metal hydroxide that contains a hydroxide mixture of 5-20 wt %, until the reaction mixture having its acid value reduced to below 0.07 mgKOH/g, and then performing removal of the residual alcohol, drying and filtration, so as to obtain the final DOTP plasticizer.

The esterification catalyst is a metal-containing catalyst and is selected from tetraisopropyl titanate (TIPT), titanium tetraisobutanolate (TIBT) or tetra 2-ethylhexyl titanate (EHT), which is removed after esterification using steam and active carbon.

Therein, water produced during the esterification and the alcohol used are formed in to an azeotrope under vacuum pressure or atmospheric pressure, and the azeotrope is removed from the reaction mixture.

And, the aqueous solution of alkaline metal hydroxide is used excessively, namely in an amount equal to 4-5 times as required by the acid value of the reaction mixture.

The low-odor DOTP plasticizer made using the method of the present invention has the reaction efficiency in a process for producing the DOTP plasticizer increased by more than one time, and, due to significantly decrease of the esterification, had their reaction time reduced at least 37.5% over the existing technology.

In the present invention, the reaction components for esterification are PTA and a C6-C10 alcohol. Therein, the alcohol comprises 2-ethylhexanol (2-EH), isononyl alcohol, and isodecyl alcohol.

DOTP plasticizers made through esterification in the following examples and comparative examples were tested for their physical properties using the measurement methods described below:

1. The odor level was analyzed using an odor analyzer modeled Alpha MOS E-NOSE Heracles II.
2. The particle size of PTA was analyzed using a particle size distribution analyzer (LS13320).
3. The specific surface area of PTA samples was measured using a high-definition micromeritics surface area and porosity analyzer BET (ASAP 2020). The samples were weighted to be 0.1-0.3 g for analysis.

Example 1

Figure 2:
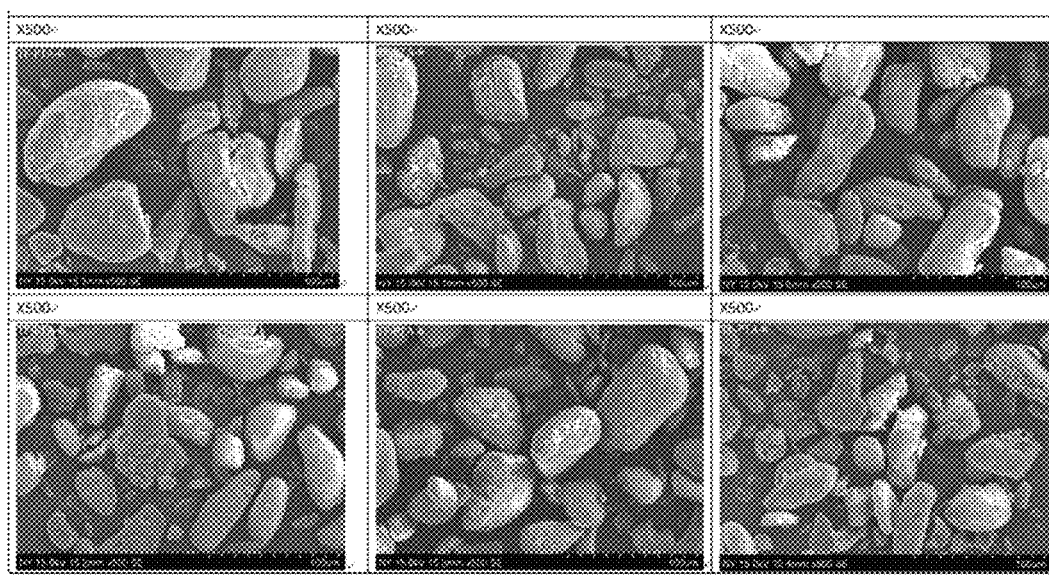
FIG. 2 is a SEM image of PTA that has been fined for six times with homogenizer.

The components used are shown in Table 1. First, a homogenizer was used to fine the PTA composition as below. 119 g of PTA and 119 g of a slurry solvent 2-EH were mixed and processed using the homogenizer (3000-6000 rpm, 50-60 Hz) for 6 times into slurry (1) to form PTA slurry having a PTA particle size of 107.3 μm. The SEM image of PTA was shown in FIG. 2. Additional 161 g of the alcohol, 2-EH, was used to rinse residual PTA slurry in the homogenizer to obtain slurry (2). And, 0.6 g of TIPT as a catalyst was added into the slurry (1) and the slurry (2) in a four-neck flask. With nitrogen gas introduced, the reaction temperature was increased gradually from 180° C. to 225° C. over the reaction time of 2.5 hours, including the reaction pressure was 1013 mbar for the first 1.5 hours and −30 mbar for the last 1 hour, with water produced during the reaction removed. When the acid value of the mixture became below 1 mgKOH/g, an aqueous solution of alkaline metal hydroxide was used for neutralization until the acid value of the mixture became below 0.07 mgKOH/g. Then distillation was performed to reduce the content of the alcohol to 300 μm or less. The process was finalized by filtration and purification. The result is provided in Table 1.

Example 2

The components both used and processed are same as described for Example 1, except the slurry (1) is processed for 9 times through using the homogenizer to form PTA slurry having a PTA particle size of 103.2 μm, instead of 6 times taught by the Example 1. The result is provided in Table 1.

Example 3

The composition as shown in Table 1 was processed as described for Example 1, with the difference that the component weight ratio of PTA/2-EH slurry was 1:1.3, and the PTA slurry has a PTA particle size of 108.6 μm. The result is provided in Table 1.

Example 4

The composition as shown in Table 1 was processed as described for Example 2, with the difference that the component weight ratio of PTA/2-EH slurry was 1:1.5, and the PTA slurry has a PTA particle size of 103.2 μm. The result is provided in Table 1.

Example 5

The composition as shown in Table 1 was processed as described for Example 1, with the difference that the alcohol used as the esterification component was INA instead of 2-EH, and the slurry solvent was INA instead of 2-EH. The PTA slurry has a PTA particle size of 101 μm. The result is provided in Table 1.

Example 6

The composition as shown in Table 1 was processed as described for Example 2, with the difference that the alcohol used as the esterification component was INA instead of 2-EH, and the slurry solvent was INA instead of 2-EH. The PTA slurry has a PTA particle size of 82 μm. The result is provided in Table 1.

Example 7

The composition as shown in Table 1 was processed as described for Example 1, with the difference that the use amount of the catalyst was 1.0 g instead. The PTA slurry has a PTA particle size of 106.5 μm. The result is provided in Table 1.

Example 8

The composition as shown in Table 1 was processed as described for Example 1, with the difference that the component weight ratio of PTA/2-EH slurry was 1:0.8. The PTA slurry has a PTA particle size of 106.2 μm. The result is provided in Table 1.

Example 9

The composition as shown in Table 1 was processed as described for Example 1, with the difference that the component weight ratio of PTA/2-EH slurry was 1:0.9. The PTA slurry has a PTA particle size of 107.2 μm. The result is provided in Table 1.

Comparative Example 1

The composition as shown in Table 1 was processed as described for Example 1, but PTA (particle size of 141.2 μm) whose SEM image was shown in FIG. 1 was not fined using a homogenizer.

119 g of PTA, 280 g of 2-EH and 0.6 g of TIPT as a catalyst were placed in a four-neck flask. With nitrogen gas introduced, the reaction temperature was increased gradually from 180° C. to 225° C. over the reaction time, where the reaction pressure was 1013 mbar for the first 4.5 hours and −30 mbar for the last 1 hour, with water produced during the reaction removed. When the acid value of the mixture became below 1 mgKOH/g, an aqueous solution of alkaline metal hydroxide was used for neutralization until the acid value of the mixture became below 0.07 mgKOH/g. Then distillation was performed to reduce the content of the alcohol to 300 ppm or less. The process was finalized by filtration and purification. The result is provided in Table 1.

Comparative Example 2

The composition as shown in Table 1 was processed as described for Comparative Example 1, with the difference that the PTA had a particle size of 100.3 μm instead of 141.2 μm.

Comparative Example 3

The composition as shown in Table 1 was processed as described for Comparative Example 1, with the difference that PTA had a particle size of 120.4 μm instead of 141.2 μm.

TABLE 1

Compositions and Odor Analysis of Examples and Comparative Examples

| | | | | Example | | | | | |
|---|---|---|---|---|---|---|---|---|---|
| | | | | 1 | 2 | 3 | 4 | 5 | 6 |
| Synthesis components | Weight ratio of components of PTA slurry [1] | | | 1:1 | 1:1 | 1:1.3 | 1:1.5 | 1:1 | 1:1 |
| | Alcohol | 2-EH (g) | Total weight [2] | 280 | 280 | 280 | 280 | — | — |
| | | | Extra addition | 161 | 161 | 125.3 | 101.5 | 0 | 0 |
| | | INA (g) | Total weight [2] | 0 | 0 | 0 | 0 | 310 | 310 |
| | | | Extra addition | 0 | 0 | 0 | 0 | 191 | 191 |
| | Catalyst | TIPT (g) | | 0.6 | 0.6 | 0.6 | 0.6 | 0.6 | 0.6 |
| | PTA | PTA (g) | | 119 | 119 | 119 | 119 | 119 | 119 |
| | Slurry | Slurry solvent | 2-EH (g) | 119 | 119 | 154.7 | 178.5 | 0 | 0 |
| | | | INA (g) | 0 | 0 | 0 | 0 | 119 | 119 |
| | | No. of times fined in homogenizer | | 6 | 9 | 6 | 9 | 6 | 9 |
| | | D50 (μm) | Average particle size of PTA | 107.3 | 103.2 | 108.6 | 103.2 | 101 | 82 |
| | | BET SSA analysis (m2/g) | Specific Surface Area (SSA) | 0.3795 | 0.3816 | 0.3780 | 0.3812 | 0.3723 | 0.3653 |
| | | | Increase rate of SSA (%) [3] | 9.3 | 9.9 | 8.87 | 9.79 | 7.23 | 5.21 |
| Total weight of final PTA plasticizer (g) | | | | 279.55 | 279.55 | 279.55 | 279.55 | 299.62 | 299.62 |
| Esterification time (hours) | | | | 2.5 | 2.5 | 2.5 | 2.5 | 2.5 | 2.5 |
| Odor [4] | | | | Level 3 | Level 3 | Level 3 | Level 3 | Level 3 | Level 3 |

| | | | | Example | | | Comparative Example | | |
|---|---|---|---|---|---|---|---|---|---|
| | | | | 7 | 8 | 9 | 1 | 2 | 3 |
| Synthesis components | Weight ratio of components of PTA slurry [1] | | | 1:1 | 1:0.8 | 1:0.9 | — | — | — |
| | Alcohol | 2-EH (g) | Total weight [2] | 280 | 280 | 280 | 280 | 280 | 280 |
| | | | Extra addition | 161 | 184.8 | 172.9 | 0 | 0 | 0 |
| | | INA (g) | Total weight [2] | 0 | 0 | 0 | 0 | 0 | 0 |
| | | | Extra addition | 0 | 0 | 0 | 0 | 0 | 0 |
| | Catalyst | TIPT (g) | | 1.0 | 0.6 | 0.6 | 0.6 | 0.6 | 0.6 |
| | PTA | PTA (g) | | 119 | 119 | 119 | 119 | 119 | 119 |
| | Slurry | Slurry solvent | 2-EH (g) | 119 | 95.2 | 107.1 | 0 | 0 | 0 |
| | | | INA (g) | 0 | 0 | 0 | 0 | 0 | 0 |
| | | No. of times fined in homogenizer | | 6 | 6 | 6 | 0 | 0 | 0 |
| | | D50 (μm) | Average particle size of PTA | 106.5 | 106.2 | 107.2 | 141.2 | 100.3 | 120.4 |

TABLE 1-continued

|  |  |  |  |  |  |  |  |
|---|---|---|---|---|---|---|---|
| BET SSA analysis $(m^2/g)$ | Specific Surface Area (SSA) | 0.3801 | 0.3796 | 0.3799 | 0.3472 | 0.3572 | 0.3485 |
|  | Increase rate of SSA (%) [3] | 9.47 | 9.3 | 9.4 | 0 | 0 | 0 |
| Total weight of final PTA plasticizer (g) | | 279.55 | 279.55 | 279.55 | 279.55 | 279.55 | 279.55 |
| Esterification time (hours) | | 2.5 | 2.5 | 2.5 | 5.5 | 4 | 4 |
| Odor [4] | | Level 3 | Level 3 | Level 3 | Level 4.5 | Level 4 | Level 4 |

Note:
1. The weight ratio of the components of the slurry is the ratio of PTA to the slurry solvent.
2. Total weight of alcohol in formula is the sum of alcohol in slurry solvent and extra added alcohol.
For example:
[1] The total weight of the alcohol (280 g) in the formula of Example 1 is the sum of slurry solvent (2-EH of 119 g) and extra addition (2-EH of 161 g).
[2] The total weight of the alcohol (280 g) in the formula of Example 3 is the sum of slurry solvent (2-EH of 154.7 g) and extra addition (2-EH of 125.3 g).
[3] The total weight of the alcohol (310 g) in the formula of Example 5 is the sum of slurry solvent (INA of 119 g) and extra addition (INA of 191 g).
[4] The total weight of the alcohol (280 g) in the formula of Example 8 is the sum of slurry solvent (2-EH of 95.2 g) and extra addition (2-EH of 184.8 g).
3. Increase rate of Specific Surface Area (SSA) in percentage (%):
The increase of SSA in percentage (%) may be determined by dividing the difference obtained through S2 minus S1 by the S1.
Wherein S1 is the SSA of non-fined PTA (i.e. specific surface area of Comparative Example 1); and S2 is the SSA of the PTA after fined with homogenizer.
For example:
[1] The increase rate of SSA of Example is 9.3% determined by dividing the difference obtained through 0.3795 minus 0.3472 by the 0.3472.
[2] The increase rate of surface area of Example 2 is 9.9% determined by dividing the difference obtained through 0.3816 minus 0.3472 by the 0.3472.
[3] The increase rates of surface area in percentage (%) of Examples 3-9 and Comparative Examples 1-3 can be calculated similarly.
4. Analysis of odor: the lower the level is, the better the odor is.

Results
1. PTA was mixed with 2-EH/PTA or INA/PTA at a ratio of 1:0.8-1.5 as listed in Table 1 to form slurry, and the slurry was fined with additional 2-EH or INA as listed in Table 1 using a homogenizer (single-stage, 3 rotators, 3 stators) for 6 or 9 times, respectively, for esterification directly, with the attempt to reduce synthesis time and thermal history and to improve odor and productivity.
2. The PTA slurry of Example 1, after processed for 6 times in the homogenizer, had its PTA particle size reduced to 107.3 μm from 141.2 μm, and had its specific surface area increased by 9.3%.
The PTA slurry of Example 2, after processed for 9 times in the homogenizer, had its PTA particle size reduced to 103.2 μm from 141.2 μm, and had its specific surface area increased by 9.9%.
The PTA slurry of Example 3, after processed for 6 times in the homogenizer, had its PTA particle size reduced to 108.6 μm from 141.2 μm, and had its specific surface area increased by 8.87%.
The PTA slurry of Example 4, after processed for 9 times in the homogenizer, had its PTA particle size reduced to 103.2 μm from 141.2 μm, and had its specific surface area increased by 9.79%.
The PTA slurry of Example 5, after processed for 6 times in the homogenizer, had its PTA particle size reduced to 101 μm from 141.2 μm, and had its specific surface area increased by 5.21%.
The PTA slurry of Example 6, after processed for 9 times in the homogenizer, had its PTA particle size reduced to 82 μm from 141.2 μm, and had its specific surface area increased by 7.23%.
The PTA slurry of Example 7, after processed for 6 times in the homogenizer, had its PTA particle size reduced to 106.5 μm from 141.2 μm, and had its specific surface area increased by 9.47%.
The PTA slurry of Example 8, after processed for 6 times in the homogenizer, had its PTA particle size reduced to 106.2 μm from 141.2 μm, and had its specific surface area increased by 9.3%,
The PTA slurry of Example 9, after processed for 6 times in the homogenizer, had its PTA particle size reduced to 107.2 μm from 141.2 μm, and had its specific surface area increased by 9.4%.
3. The DOTP plasticizers made in the examples 1-9 had their reaction efficiency increased by more than one time, and had their reaction time reduced at least 37.5%, and were low-odor.

In comparison with Comparative Examples 1-3, the PTA slurry of each of Examples 1-9 was fined using a homogenizer and then put into esterification according to the composition as provided in Table 1, its esterification time was shortened to 2.5 hours when compared to 4-5.5 hours required for Comparative Examples 1-3, i.e., capable of reducing reaction time by 37.5-54.5% in process for producing the DOTP plasticizer; and, the resulting DOTP plasticizer of each of Examples 1-9 is a low-odor plasticizer, which odor level was reduced to Level 3, when compared to Level 4 or Level 4.5 belong to Comparative Examples 1-3.
4. The plasticizer of Example 6 began to agglutinate when the particle size was below 82 μm, and the increase rate of surface area was only 5.21%, demonstrating that further fining would be inappropriate.

What is claimed is:
1. A method for use in enhancing reaction efficiency for producing a terephthalate plasticizer, comprising steps of:
 (1) mixing a purified terephthalic acid (PTA) and a C6-C10 alcohol in a weight ratio of 1:0.8-1.5 and processed in a homogenizer for 2-8 hours so as to form a PTA slurry having a PTA particle size between 80 and 110 μm and a specific surface area at least 0.3723 $m^2/g$, wherein increase rate of the specific surface area is between 5 and 10%;
 (2) providing 75-107 wt % of the PTA slurry of Step (1) and 30-85 wt % of the C6-C10 alcohol, both based on a total weight of the terephthalate plasticizer of Step (5);
 (3) providing 0.1-2.0 wt % of a titanium-based catalyst as an esterification catalyst, based on the total weight of the terephthalate plasticizer of Step (5);
 (4) esterifying the components of Step (2) with the presence of the esterification catalyst of Step (3) at a pressure of between −30 and 1013 mbar and a temperature of between 200 and 250° C. for 2-3 hours to form a reaction mixture;

(5) after esterification, neutralizing the reaction mixture with an aqueous solution of alkaline metal hydroxide that contains a 5-20 wt % of hydroxide mixture, until the reaction mixture having its acid value reduced to below 0.07 mgKOH/g, and then removing the residual C6-C10 alcohol, drying and filtration, so as to obtain the terephthalate plasticizer;

wherein the C6-C10 alcohol is selected from 2-ethylhexanol (2-EH), isononyl alcohol (INA), and isodecyl alcohol.

2. The method of claim 1, wherein the titanium-based catalyst is one or more selected from the group consisting of tetraisopropyl titanate (TIPT), titanium tetraisobutanolate (TIBT) and tetra 2-ethylhexyl titanate (EHT).

3. The method of claim 1, wherein water produced during the esterification and the alcohol used are formed in to an azeotrope under vacuum pressure or atmospheric pressure, and the azeotrope is removed from the reaction mixture.

4. The method of claim 1, wherein the esterification catalyst is removed after esterification using steam and active carbon.

5. The method of claim 1, wherein the aqueous solution of alkaline metal hydroxide in Step (5) is in an amount of 4-5 times exceeding what is required by the acid value of the reaction mixture.

6. The method of claim 1, wherein the PTA particles size between 100 and 110 μm.

* * * * *